(12) United States Patent
Miller et al.

(10) Patent No.: US 8,685,095 B2
(45) Date of Patent: Apr. 1, 2014

(54) EXPANDABLE IMPLANT SYSTEM AND METHODS OF USE

(75) Inventors: Keith E. Miller, Germantown, TN (US); Sachin P. Budhabhatti, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 240 days.

(21) Appl. No.: 13/090,012

(22) Filed: Apr. 19, 2011

(65) Prior Publication Data

US 2012/0271422 A1 Oct. 25, 2012

(51) Int. Cl.
*A61F 2/44* (2006.01)

(52) U.S. Cl.
USPC ...................................... 623/17.11

(58) Field of Classification Search
USPC .......................... 623/17.11–17.16
See application file for complete search history.

(56) References Cited

U.S. PATENT DOCUMENTS

| | | |
|---|---|---|
| 5,658,336 A | 8/1997 | Pisharodi |
| 5,665,122 A | 9/1997 | Kambin |
| 5,980,522 A | 11/1999 | Koros et al. |
| 6,299,642 B1 | 10/2001 | Chan |
| 6,491,724 B1 | 12/2002 | Ferree |
| 6,835,206 B2 | 12/2004 | Jackson |
| 6,955,691 B2 | 10/2005 | Chae et al. |
| 7,320,555 B2 | 1/2008 | Chang et al. |
| 7,410,501 B2 | 8/2008 | Michelson |
| 7,445,636 B2 | 11/2008 | Michelson |
| 7,621,960 B2 | 11/2009 | Boyd et al. |
| 7,655,027 B2 | 2/2010 | Michelson |
| 7,763,078 B2 | 7/2010 | Peterman et al. |
| 7,846,185 B2 | 12/2010 | Carls et al. |
| 2004/0010315 A1 | 1/2004 | Song |
| 2004/0249466 A1 | 12/2004 | Liu et al. |
| 2005/0113916 A1 | 5/2005 | Branch, Jr. |
| 2005/0113917 A1 | 5/2005 | Chae et al. |
| 2006/0206207 A1* | 9/2006 | Dryer et al. ................. 623/17.11 |
| 2006/0247778 A1 | 11/2006 | Ferree et al. |
| 2007/0191951 A1* | 8/2007 | Branch, Jr. ................. 623/17.11 |
| 2008/0058938 A1 | 3/2008 | Mujwid |
| 2009/0204218 A1* | 8/2009 | Richelsoph ................. 623/17.16 |
| 2011/0029082 A1 | 2/2011 | Hall |

* cited by examiner

*Primary Examiner* — David Bates

(57) ABSTRACT

A spinal implant includes a first component defining a surface. A second component is movable relative to the first component and defines a surface. An intermediate component is engageable with the first component and the second component. The intermediate component is configured for relative movement along the surface of the second component and is configured for relative movement along the surface of the first component in a first axial direction and a second, opposite axial direction such that movement of the intermediate component moves the second component relative to the first component between a first configuration and a second configuration. Methods of use are disclosed.

17 Claims, 17 Drawing Sheets

EXPANDABLE IMPLANT SYSTEM AND METHODS OF USE

TECHNICAL FIELD

The present disclosure generally relates to medical devices, systems and methods for the treatment of musculoskeletal disorders, and more particularly to an interbody implant system and method that provides stabilization and height restoration for treating a vertebral column.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility. For example, after a disc collapse, severe pain and discomfort can occur due to the pressure exerted on nerves and the spinal column.

Non-surgical treatments, such as medication, rehabilitation and exercise can be effective, however, may fail to relieve the symptoms associated with these disorders. Surgical treatment of these spinal disorders includes fusion, fixation, discectomy, laminectomy and implantable prosthetics. These treatments may employ interbody implants. This disclosure describes an improvement over these prior art technologies.

SUMMARY OF THE INVENTION

Accordingly, an interbody implant system and method is provided that provides stabilization and height restoration for treating a vertebral column. It is contemplated that the interbody implant system includes a spinal implant, which is expandable between a first configuration and a second configuration. It is further contemplated that the implant system and method may be employed for an arthrodesis treatment using minimally invasive and percutaneous techniques.

In one embodiment, a spinal implant is provided. The spinal implant includes a first component defining a surface. A second component is movable relative to the first component and defines a surface. An intermediate component is engageable with the first component and the second component. The intermediate component is configured for relative movement along the surface of the second component and is configured for relative movement along the surface of the first component in a first axial direction and a second, opposite axial direction such that movement of the intermediate component moves the second component relative to the first component between a first configuration and a second configuration.

In one embodiment, an interbody implant system is provided. The spinal implant system includes a spinal implant. The spinal implant includes a first arm defining a surface extending between a first end and a second end. The surface includes an elongated ridge. A second arm defines a surface extending between a first end and a second end. The first end of the second arm is pivotably connected to the first end of the first arm. The surface of the second arm includes a slot. A wedge defines a cavity and is engageable with the first arm and the second arm. The wedge includes a protrusion configured for relative slidable movement along the slot and defines a groove configured for relative slidable movement along the ridge such that movement of the wedge rotates the second arm relative to the first arm between a collapsed configuration and an expanded configuration of the spinal implant. The spinal implant system also includes an instrument that includes an engagement member, which is engageable with the cavity to cause movement of the wedge.

In one embodiment, the spinal implant system has a spinal implant, which includes a first bifurcated arm extending between a first end and a second end. The first arm includes a surface that defines an inner cavity and an elongated ridge extending along a longitudinal axis thereof. The second end defines a cavity. A second bifurcated arm extends between a first end and a second end. The second arm includes a surface that defines an inner cavity and a slot. The first end of the second arm is pivotably connected to the first end of the first arm via an expandable bifurcated hinge. A wedge defines a cavity and is disposed with the first arm and the second arm such that at least a portion thereof is disposed within the inner cavities of the components. The wedge includes a protrusion configured for relative slidable movement along the slot and defines a groove configured for relative slidable movement along the ridge such that movement of the wedge rotates the second arm relative to the first arm between a collapsed configuration and an expanded configuration such that the spinal implant expands in a plurality of orientations relative to the longitudinal axis. An instrument includes a first engagement member and a second engagement member coaxially disposed with the first engagement member. The first engagement member is engageable with the cavity of the wedge and the second engagement member is engageable with the cavity of the first arm such that the second engagement member axially facilitates movement of the wedge relative to the first arm in a first axial direction and a second opposite axial direction between the collapsed configuration and the expanded configuration.

BRIEF DESCRIPTION OF THE DRAWINGS

The present disclosure will become more readily apparent from the specific description accompanied by the following drawings, in which.

DETAILED DESCRIPTION OF THE INVENTION

Figure 1:
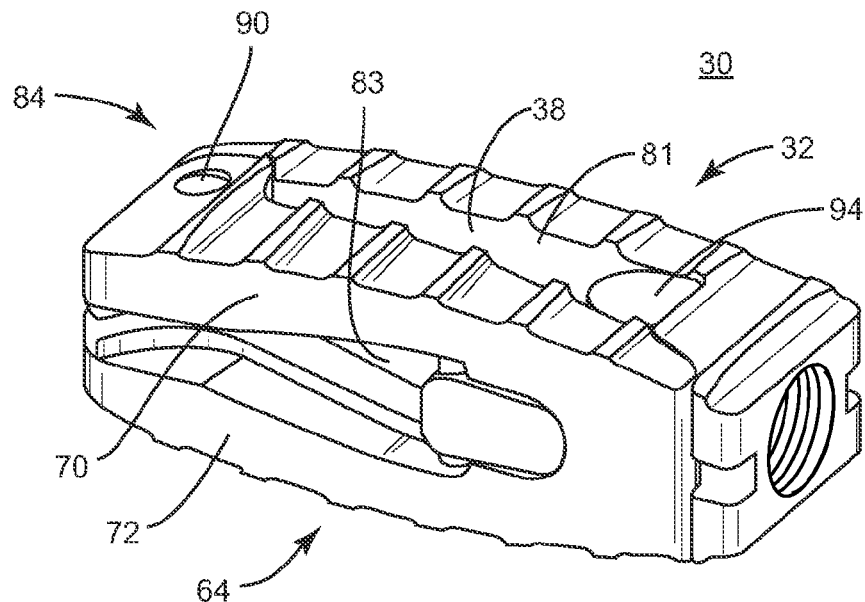
FIG. 1 is a perspective view of one particular embodiment of a spinal implant of a system in accordance with the principles of the present disclosure.
Figure 2:
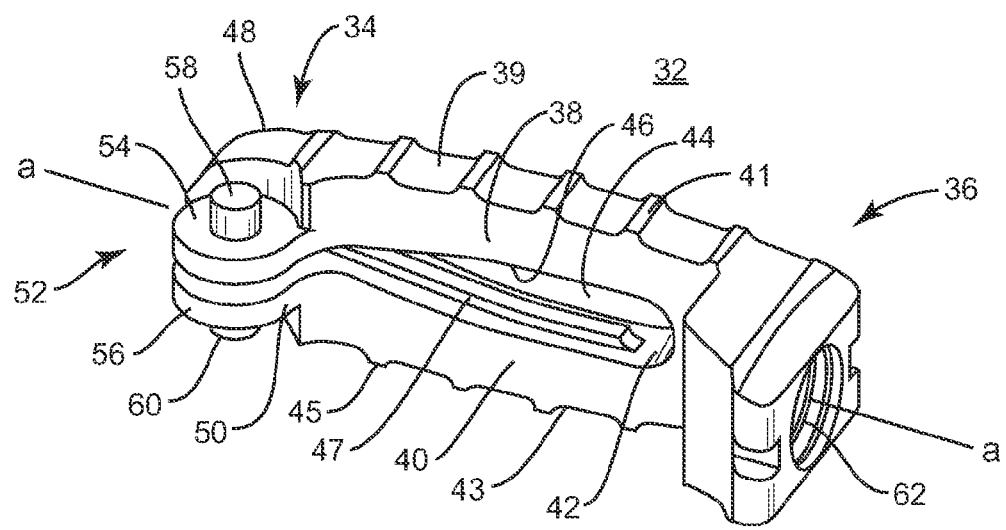
FIG. 2 is a perspective view of a first component of the spinal implant shown in FIG. 1.
Figure 3:
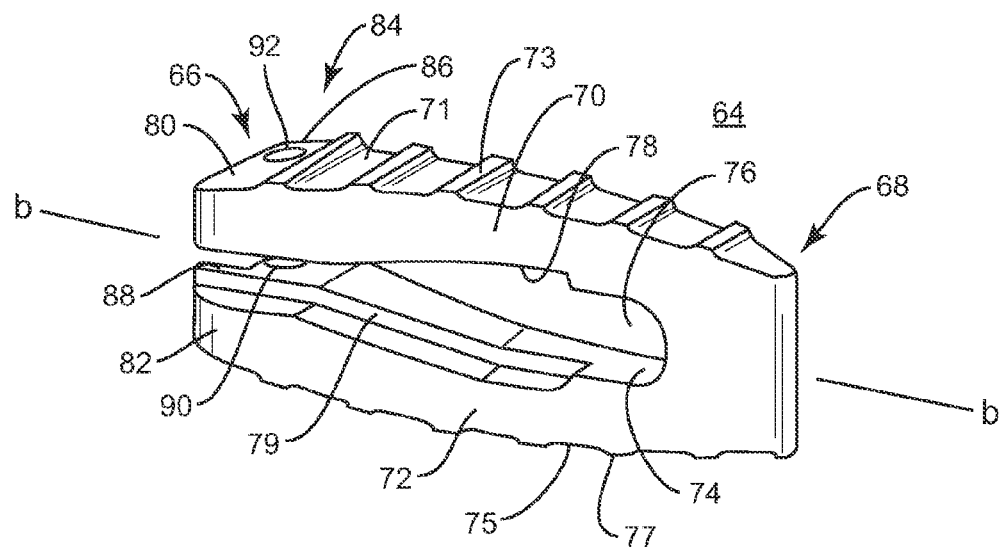
FIG. 3 is a perspective view of a second component of the spinal implant shown in FIG. 1.
Figure 4:
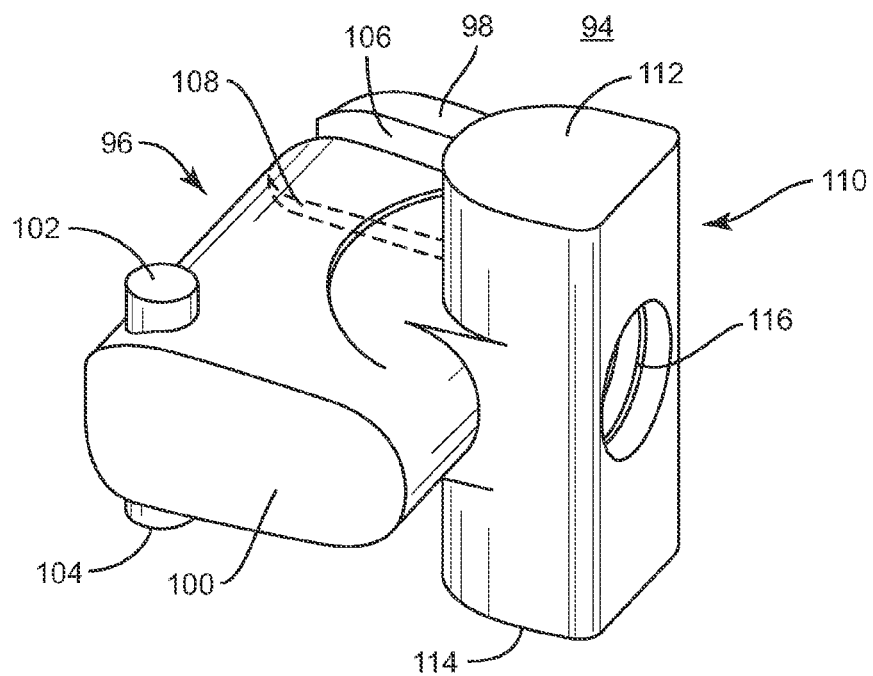
FIG. 4 is an enlarged perspective view of an intermediate component of the spinal implant shown in FIG. 1.
Figure 5:
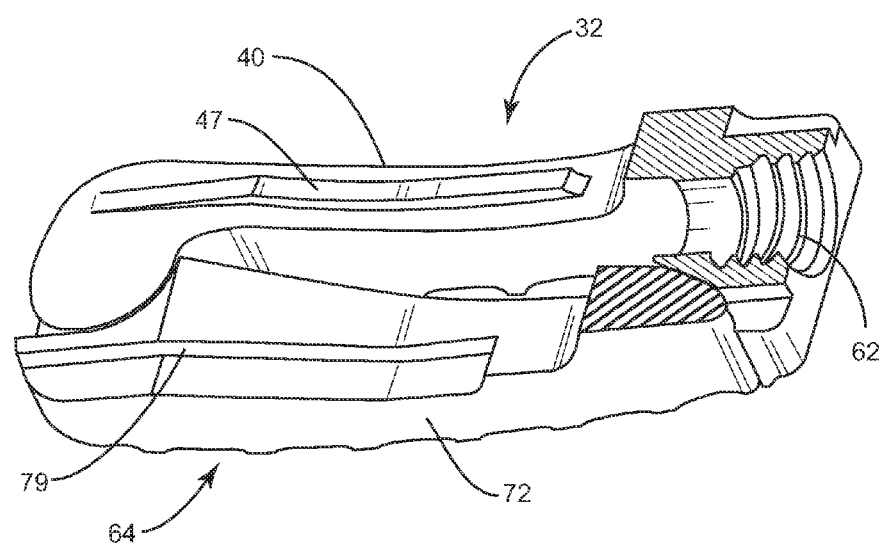
FIG. 5 is a perspective cutaway view of the spinal implant shown in FIG. 1.
Figure 6:
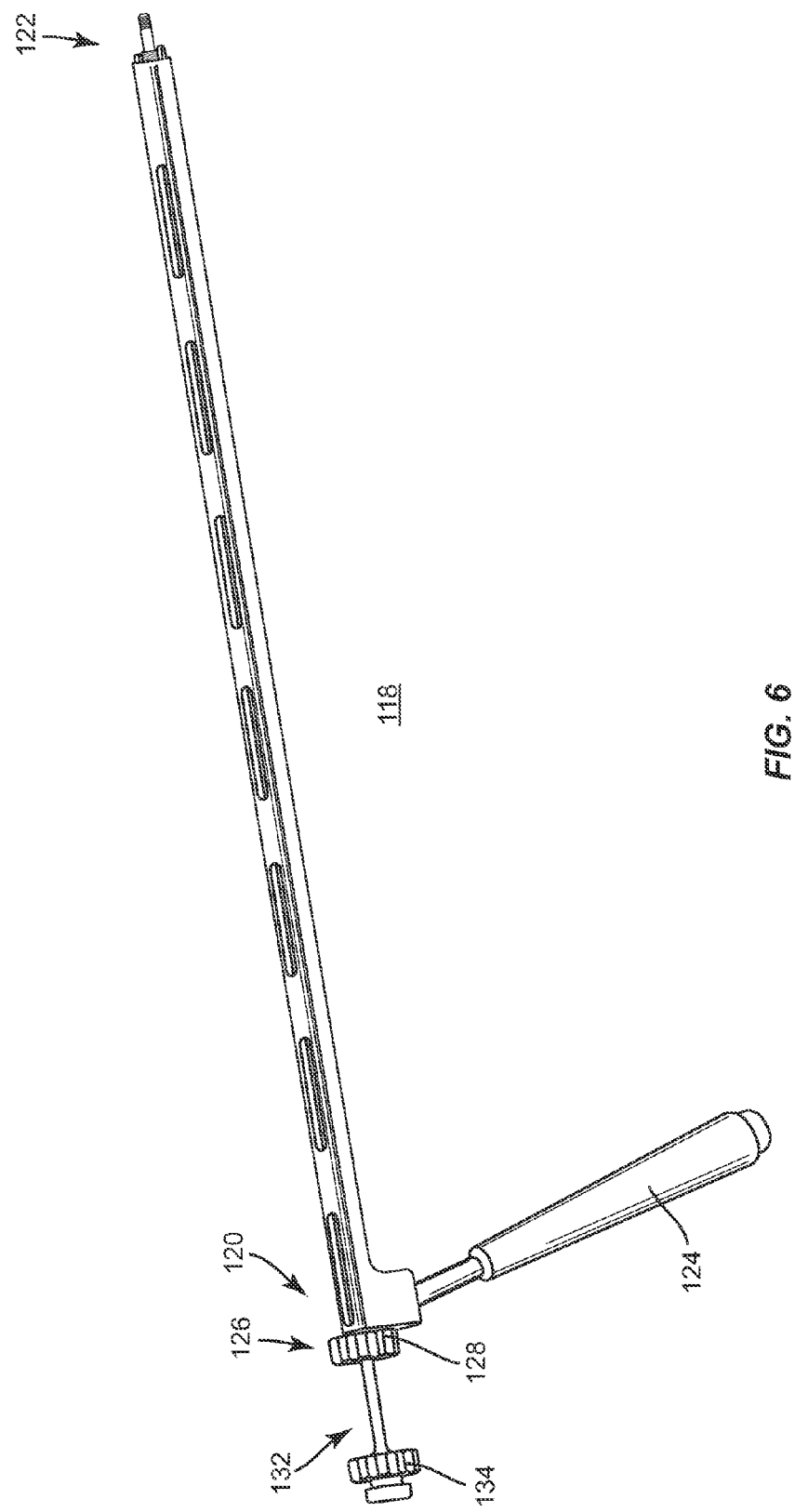
FIG. 6 is a perspective view of an instrument of the system in accordance with the principles of the present disclosure.
Figure 7:
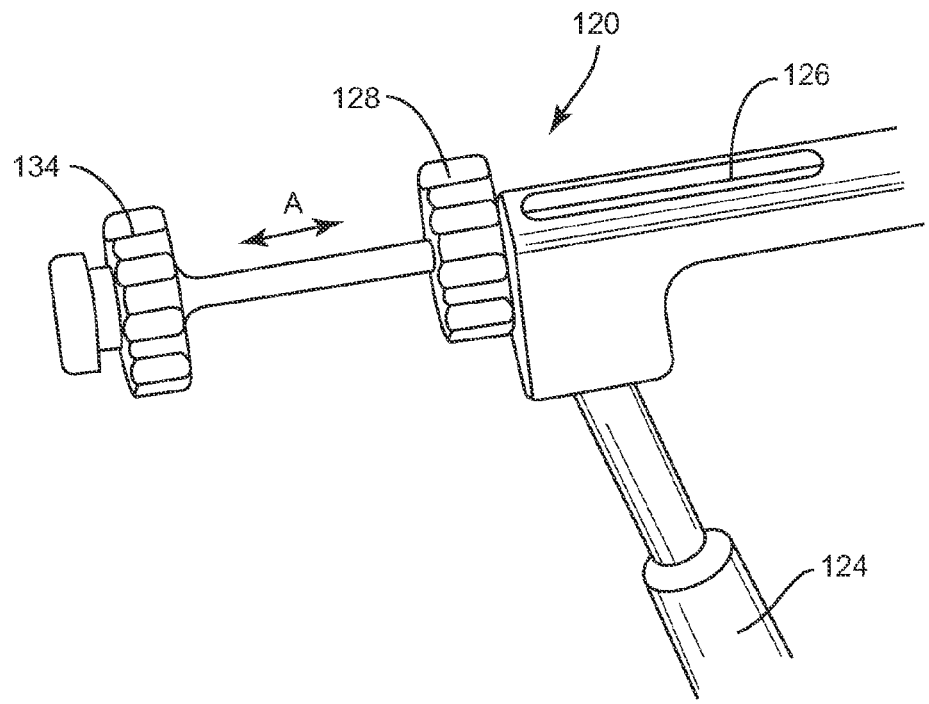
FIG. 7 is a perspective break away view of the instrument shown in FIG. 6.
Figure 8:
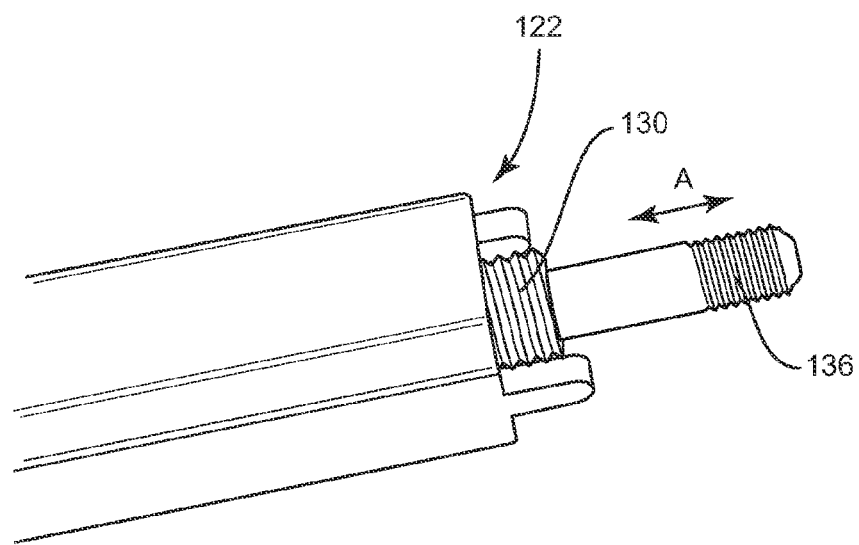
FIG. 8 is a perspective break away view of the instrument shown in FIG. 6.
Figure 9:
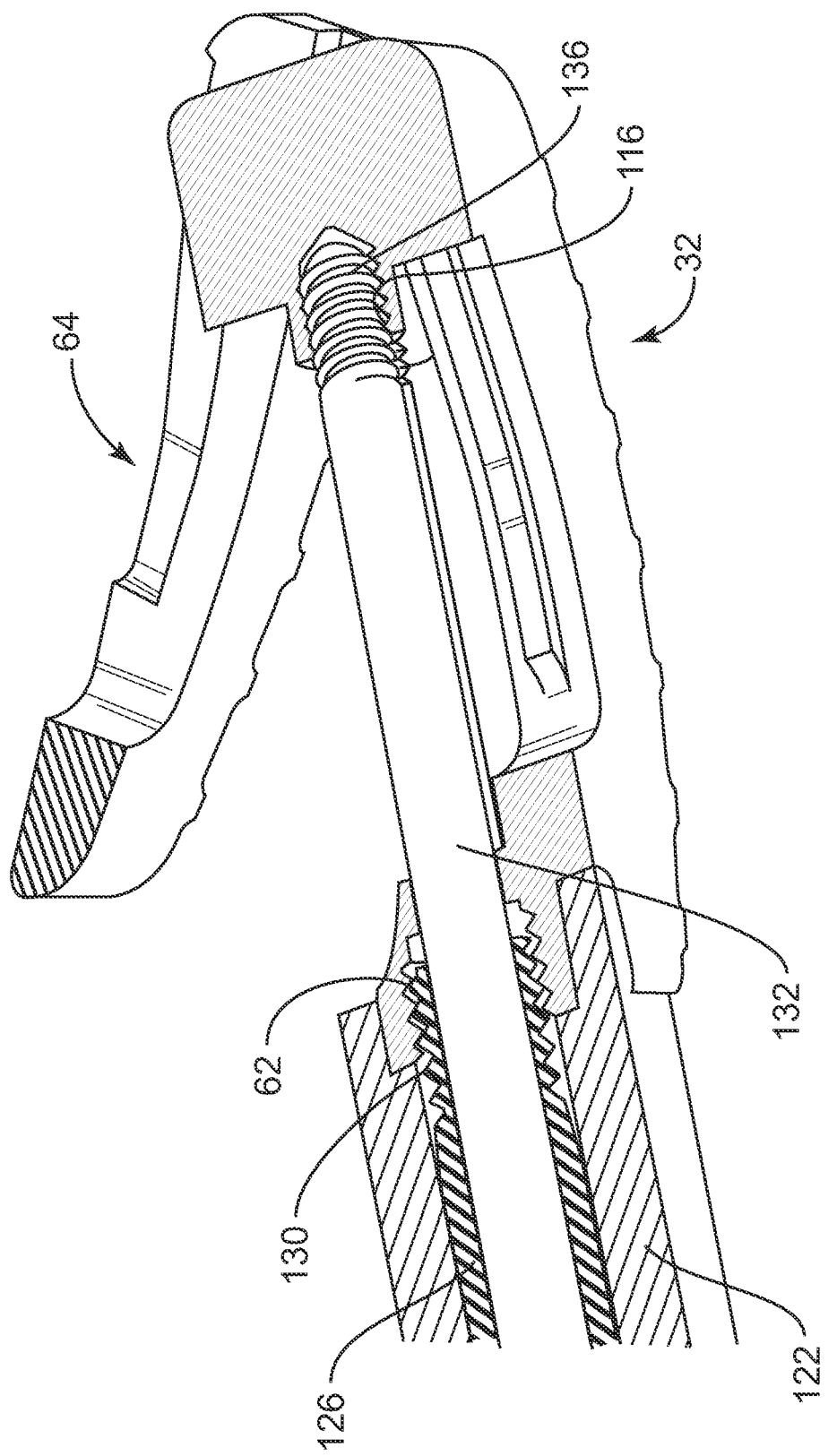
FIG. 9 is a perspective break and cut away view of the spinal implant shown in FIG. 1 connected with the instrument shown in FIG. 6.

The exemplary embodiments of the interbody implant system and related methods of use disclosed are discussed in terms of medical devices for the treatment of musculoskeletal disorders and more particularly, in terms of an interbody implant that provides stabilization and height restoration for treating a vertebral column. It is envisioned that the interbody implant system may be employed for fusion and fixation treatments to provide decompression, restoration of lordosis and/or resistance of subsidence into vertebral endplates. It is further envisioned that the interbody implant system and methods of use disclosed can be employed to obtain fusion of vertebrae through a minimally invasive or percutaneous technique. It is contemplated that the interbody implant is removable and/or may be repositioned. In one embodiment, the disclosed interbody implant system and methods of use can provide improved spinal treatment with a device that expands in a plurality of orientations including for example height to achieve decompression and the restoration of lordosis, while also expanding laterally to resist subsidence.

It is envisioned that the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is contemplated that the present disclosure may be employed with other osteal and bone related applications, including those associated with diagnostics and therapeutics. It is further contemplated that the disclosed interbody implant system may be alternatively employed in a surgical treatment with a patient in a prone or supine position, and/or employ various surgical approaches to the spine, including anterior, posterior, posterior mid-line, medial, lateral, postero-lateral, and/or antero-lateral approaches, and in other body regions. The present disclosure may also be alternatively employed with procedures for treating the lumbar, cervical, thoracic and pelvic regions of a spinal column. The interbody implant system and methods of the present disclosure may also be used on animals, bone models and other non-living substrates, such as, for example, in training, testing and demonstration.

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "superior" and "inferior" are relative and used only in the context to the other, and are not necessarily "upper" and "lower".

Further, as used in the specification and including the appended claims, "treating" or "treatment" of a disease or condition refers to performing a procedure that may include administering one or more drugs to a patient in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of an interbody implant system and related methods of employing the interbody implant system in accordance with the principles of the present disclosure. Alternate embodiments are also disclosed. Reference will now be made in detail to the exemplary embodiments of the present disclosure, which are illustrated in the accompanying figures. Turning now to FIGS. 1-5, there is illustrated components of an interbody implant system in accordance with the principles of the present disclosure.

The components of the interbody implant system can be fabricated from biologically acceptable materials suitable for medical applications, including metals, synthetic polymers, ceramics and bone material and/or their composites, depending on the particular application and/or preference of a medical practitioner. For example, the components of the interbody implant system, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKEL-ITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of the interbody implant system may have material composites, including the above materials, to achieve various desired characteristics such as strength, rigidity, elasticity, compliance, biomechanical performance, durability and radiolucency or imaging preference. The components of the interbody implant system, individually or collectively, may also be fabricated from a heterogeneous material such as a combination of two or more of the above-described materials.

The interbody implant system includes a spinal implant 30 employed as a stabilization device in fusion and fixation procedures, for example, for patients suffering from a spinal disorder to provide height restoration between vertebral bodies, decompression, restoration of lordosis and/or resistance of subsidence into vertebral endplates. The components of the interbody implant system may be monolithically formed, integrally connected or include fastening elements and/or instruments, for example, as described herein.

Spinal implant 30 includes a first component, such as, for example, a first bifurcated arm 32 extending between a first end 34 and a second end 36. Arm 32 includes a first extension 38 and a second extension 40 extending from second end 36 in a cantilevered configuration along a longitudinal axis a. Extensions 38, 40 flexibly extend from second end 36 to facilitate pivoting and/or rotation of extensions 38, 40 relative to second end 36. Extensions 38, 40 are monolithically formed with second end 36. It is envisioned that extensions 38, 40 may be alternatively connected to second end 36 by integral connection, press fit, threaded, adhesive and/or fastening elements such as hinge, clip and/or screws.

Extensions 38, 40 each have an arcuate configuration and are disposed in an opposing, substantially parallel orientation relative to axis a in the first configuration, described below. It is contemplated that extensions 38, 40 may be disposed at alternate orientations, relative to longitudinal axis a, for example, perpendicular and/or other angular orientations such as acute or obtuse, co-axial and/or may be offset or staggered. It is envisioned that extensions 38, 40 may extend in alternate configurations such as, for example, alternative radius of curvature, linear, offset and/or staggered. It is further envisioned that extensions 38, 40 may have alternate cross section configurations, such as, for example, oval, oblong, triangular, rectangular, square, polygonal, irregular, uniform, non-uniform, variable, hollow and/or tapered.

Extensions 38, 40 include a surface 42 that defines an inner cavity 44. Surface 42 is substantially smooth or even. It is envisioned that all or only a portion of surface 42 may have alternate surface configurations, such as, for example, rough, arcuate, undulating, mesh, porous, semi-porous, dimpled, polished and/or textured according to the requirements of a particular application. Cavity 44 is elongated along axis a, and expands and collapses with spinal implant 30, as will be described. It is contemplated that cavity 44 may have alternate cross section configurations such as those alternatives described herein.

The portion of surface 42 disposed with extension 38 defines a wall, such as, for example, an elongated ridge 46, which extends along axis a. The portion of surface 42 disposed with extension 40 defines a wall, such as, for example, an elongated ridge 47, which extends along axis a. Ridges 46, 47 are raised from surface 42 and extend in a substantially linear configuration along the curvature of extensions 38, 40 and cavity 44. It is envisioned that ridges 46, 47 may extend in alternate configurations such as those alternatives described herein.

Extension 38 defines a vertebra engaging surface 39, which includes a plurality of raised elements 41 configured to enhance fixation and/or gripping with vertebral tissue. Extension 40 defines a vertebra engaging surface 43, which includes a plurality of raised elements 45 configured to enhance fixation and/or gripping with vertebral tissue. Elements 41, 45 are disposed transverse to axis a. It is envisioned that surfaces 39, 43 may have alternate surface configurations to enhance fixation with tissue such as those alternatives described herein. It is further envisioned that elements 41, 45 may be disposed at alternate orientations, relative to axis a, such as those alternatives described herein.

First end 34 includes spaced apart end portions 48, 50 of extensions 38, 40, respectively. End portions 48, 50 are substantially flat or planar and define a portion of cavity 44. First end 34 includes an expandable bifurcated hinge 52. Hinge 52 includes a disc 54 extending from end portion 48 and a disc 56 extending from end portion 50. Discs 54, 56 are disposed in spaced apart parallel relation and include protrusions 58, 60, respectively, configured for connection with a second component, described below. End portions 48, 50 and hinge 52 expand and collapse with spinal implant 30, as will be described. Second end 36 defines a cavity, such as, for example, threaded opening 62 that is configured for engagement with an instrument, as described below. It is contemplated that opening 62 may be configured for alternative fastening with the instrument, such as press fit or friction fit.

Spinal implant 30 includes a second component, such as, for example, a second bifurcated arm 64, which extends between a first end 66 and a second end 68. Arm 64 includes a first extension 70 and a second extension 72 extending from second end 68 in a cantilevered configuration along an axis b, which is disposed relative to axis a as a component of spinal implant 30. Extensions 70, 72 flexibly extend from second end 68 to facilitate pivoting and/or rotation of extensions 70, 72 relative to second end 68. Extensions 70, 72 are monolithically formed with second end 68. It is envisioned that extensions 70, 72 may be alternatively connected to second end 68 such as those alternatives described herein.

Extensions 70, 72 each have an arcuate configuration and are disposed in an opposing, substantially parallel orientation relative to axis b. It is contemplated that extensions 70, 72 may be disposed at alternate orientations relative to axis a such as those alternatives described herein. It is envisioned that extension 70, 72 may extend in alternate configurations and may have alternate cross section configurations such as those alternatives described herein.

Extensions 70, 72 include a surface 74 that defines an inner cavity 76. Surface 74 is substantially smooth or open. It is envisioned that all or only a portion of surface 74 may have alternate surface configurations, such as those alternatives described herein. Cavity 76 is elongated along axis b and expands and collapses with spinal implant 30, as will be described. It is contemplated that cavity 76 may have alternate cross section configurations such as those alternatives described herein. The portion of surface 74 disposed with extension 70 defines a passageway, such as, for example, an elongated slot 78, which extends along axis b. The portion of surface 74 disposed with extension 72 defines a passageway, such as, for example, an elongated slot 79, which extends along axis b. Slots 78, 79 are formed within surface 74 and extend in a substantially linear configuration along the curvature of extensions 70, 72 and cavity 76. It is envisioned that slots 78, 79 may extend in alternate configurations such as those described herein.

Extension 70 defines a vertebra engaging surface 71, which includes a plurality of raised elements 73 configured to enhance fixation and/or gripping with vertebral tissue. Extension 72 defines a vertebra engaging surface 75, which includes a plurality of raised elements 77 configured to enhance fixation and/or gripping with vertebral tissue. Elements 73, 77 are disposed transverse to axis b. It is envisioned that surfaces 71, 75 may have alternate surface configurations to enhance fixation with tissue such as those alternatives described herein. It is further envisioned that elements 73, 75 may be disposed at alternate orientations relative to axis b such as those alternatives described herein.

Extension 70 and extension 38 define a cavity 81 disposed therebetween. Cavity 81 is elongated and extends between the first and second ends of arms 32, 64. Extension 72 and extension 40 define a cavity 83 disposed therebetween. Cavity 83 is elongated and extends between the first and second ends of arms 32, 64.

First end 66 includes spaced apart end portions 80, 82 of extensions 70, 72, respectively. End portions 80, 82 are substantially flat or planar and define a portion of cavity 76. First end 66 includes an expandable bifurcated flange 84. Flange 84 includes a part 86 extending from end portion 80 and a part 88 extending from end portion 82. Parts 86, 88 are disposed in spaced apart parallel relation and include openings 90, 92, respectively. Openings 90, 92 receive protrusions 58, 60 such that flange 84 is movably mounted with hinge 52 to facilitate a pivoting connection between arms 32, 64. Arms 32, 64 are relatively movable, and end portions 80, 82 and flange 84 expand and collapse with spinal implant 30, as will be described. Second end 68 is rotatable, via the pivotable connection of arms 32, 64, to an angular orientation relative to axis a corresponding to the expansion of spinal implant 30. It is contemplated that arms 32, 64 may be connected via a living hinge.

An intermediate component, such as, for example, a wedge 94 is engageable with arm 32 and arm 64. Wedge 94 is disposed with arms 32, 64 such that at least a portion of wedge 94 is disposed within cavities 44, 76. Wedge 94 includes a first member 96 having wings 98, 100. Wing 98 extends through cavity 44 and is slidably supported therein by surface 42. Wing 100 extends through cavity 76 and is slidably supported therein by surface 74. First member 96 has a substantially rectangular configuration. It is envisioned that first member 96 may be alternately configured such as those alternatives described herein.

First member 96 is disposed in a plane, for example, horizontal, such that first member 96 is able to freely slide between arms 32, 64 and their respective extensions. First member 96 includes a protrusion 102 disposed on an upper surface thereof and a protrusion 104 disposed on a lower surface thereof, which are configured for relative slidable movement along slots 78, 79. First member 96 defines a cavity, such as, for example, a groove 106 disposed on the upper surface thereof and a groove 108 disposed on the lower surface thereof, which are configured for relative slidable movement along ridges 46, 47.

Wedge 94 includes a second member 110 connected with and disposed in a transverse orientation relative to first member 96. Second member 110 has ends 112, 114. End 112 extends through cavity 81 and is slidably supported therein by extensions 38, 70. Wing 114 extends through cavity 83 and is slidably supported therein by extensions 40, 72. Second member 110 is disposed in a plane, for example, transverse to the plane defined by first member 96 such as vertical, such that second member 110 is able to freely slide between arms 32, 64 and their respective extensions. Second member 110 defines a cavity, such as, for example, threaded opening 116 that is configured for engagement with an instrument, as described below.

In operation, spinal implant 30 is engaged for disposal between a first configuration and a second configuration such that spinal implant 30 expands in a plurality of orientations relative to axis a. Spinal implant 30 is engaged with an instrument 118, as shown in FIGS. 6-9, to facilitate actuation of the component parts of spinal implant 30 and disposal thereof in various configurations according to the requirements of a particular surgical application. Instrument 118 is a surgical tool for manipulating spinal implant 30. Instrument 118 extends between a first end 120 and a second end 122.

A handle 124 is disposed adjacent first end 120. Instrument 118 includes a first engagement member 126 that extends between first end 120 and second end 122. First engagement member 126 includes an actuator 128 disposed adjacent first end 120. Actuator 128 has knurled knob configuration and is rotatable relative to instrument 118 in a first direction, such as clockwise, and a second direction, such as counter clockwise. First engagement member 126 includes a threaded portion 130 disposed adjacent second end 122. Threaded portion 130 is configured to mate with threaded opening 62 in a threaded engagement. Threaded portion 130 is caused to engage opening 62 and actuator 128 is rotated in a selected direction such that portion 130 is threaded with opening 62. As such, first engagement member 126 is fixed with arm 32 so that spinal implant 30 can be positioned in a body cavity of a patient for a surgical procedure.

Instrument 118 includes a second engagement member 132, which is coaxially disposed with first engagement member 126. Second engagement member 132 includes an actuator 134 disposed adjacent first end 120. Actuator 134 has a knurled knob configuration and is rotatable relative to instrument 118 in a first direction, such as clockwise, and a second direction, such as counter clockwise. Actuator 134 is configured for translation relative to instrument 118 in a first axial direction and a second axial direction, as shown by arrows A in FIGS. 7-8.

Second engagement member 132 includes a threaded portion 136 disposed adjacent second end 122. Threaded portion 136 is configured to mate with threaded opening 116 in a threaded engagement. Threaded portion 136 is caused to engage opening 116 and actuator 134 is rotated in a selected direction such that portion 136 is threaded with opening 116. As such, second engagement member 132 is fixed with wedge 94 so that wedge 94 can be manipulated for reciprocal translational movement relative to arms 32, 64 along axis a, for disposal of spinal implant 30 between the first and second configurations.

Figure 10:
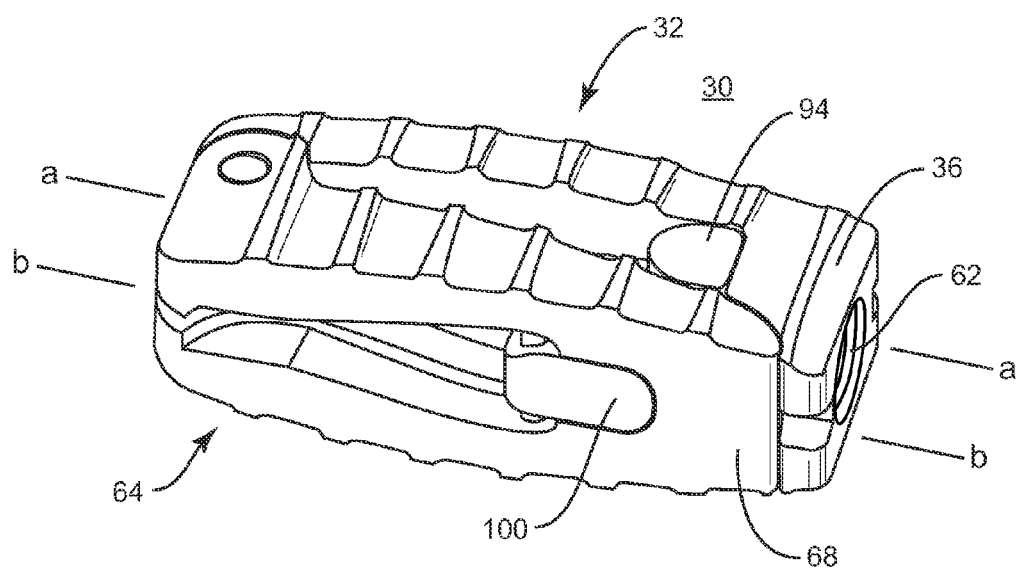
FIG. 10 is a perspective view of the spinal implant shown in FIG. 1.
Figure 11:
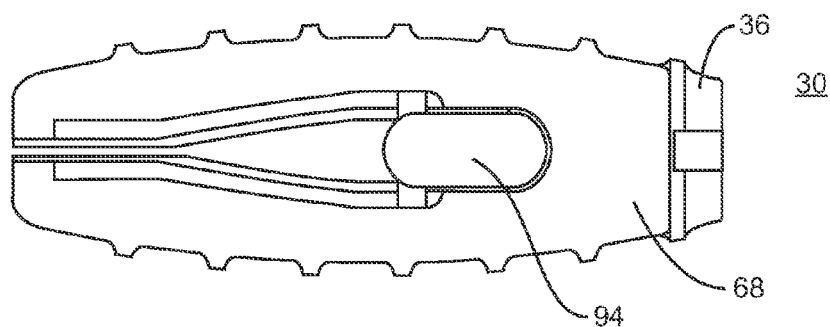
FIG. 11 is a side view of the spinal implant shown in FIG. 1.
Figure 12:
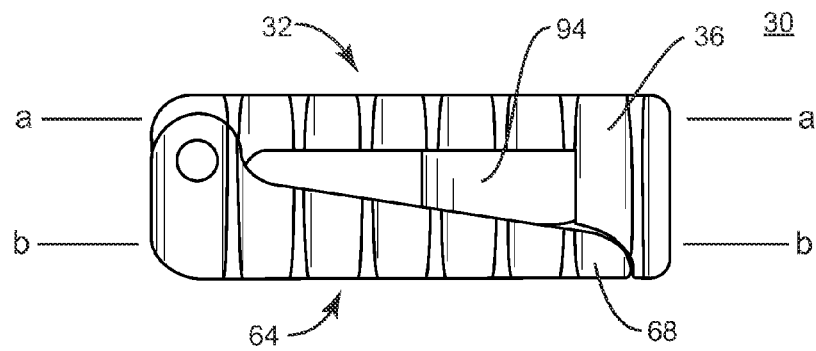
FIG. 12 is a top view of the spinal implant shown in FIG. 1.

In a first configuration, such as, for example, a collapsed configuration, as shown in FIGS. 10-12, arms 32, 64 are disposed in a low profile orientation such that axis b, corresponding to the positioning of arm 64, is disposed in substantially parallel relation to axis a, corresponding to arm 32. Second end 68 is disposed adjacent and in close proximity to second end 36. Second end 68 mates with a correspondingly configured portion of second end 36 such that spinal implant 30 has a generally rectangular configuration.

Wedge 94 is mounted within spinal implant 30 and disposed between arms 32, 64. Protrusions 102, 104 are disposed in slots 78, 79, respectively, and ridges 46, 47 are disposed within grooves 106, 108. Wings 98, 100 are disposed in a proximal most position of cavities 44, 76 and ends 112, 114 are disposed in a proximal most position of cavities 81, 83, relative to ends 36, 68. End portions 48, 50, discs 54, 56 and end portions 80, 82, respectively, are disposed adjacent and in close proximity.

Threaded portion 130 of first engagement member 126 is caused to engage opening 62 and actuator 128 is rotated in a clockwise direction such that portion 130 is threaded with opening 62. As such, first engagement member 126 is fixed with arm 32 so that spinal implant 30 can be positioned in a body cavity of a patient for a surgical procedure. Threaded portion 136 of second engagement member 132 is caused to engage opening 116 and actuator 134 is rotated in a clockwise direction such that portion 136 is threaded with opening 116. As such, second engagement member 132 is fixed with wedge 94. Actuator 134 is manipulable so that wedge 94 can be translated axially for reciprocal movement relative to arms 32, 64 along axis a.

Upon desired positioning of spinal implant 30 according to the requirements of a particular surgical application, actuator 134 is manipulated with a pushing force to drive wedge 94 axially. As wedge 94 is translated axially in a first axial direction shown by arrow B in FIGS. 13 and 15, grooves 106, 108 slidably move along ridges 46, 47 and arm 32 remains fixed in position with regard to a body cavity of a patient.

Ends 112, 114 slidably move within cavities 81, 83 to force arm 64 outwardly and to rotate, in the direction shown by arrow C, relative to arm 32. Arm 64 pivots about the connection of arm 64 with arm 32 via hinge 52. It is envisioned that arm 64 is spaced apart from arm 32 such that axis b is disposed at an angle α from axis a. It is further envisioned that angle α may be in a range of 15-90 degrees. Simultaneously, as wedge 94 is translated axially in the first axial direction, wings 98, 100 translate axially through cavities 44, 76 and engage surfaces 42, 74, respectively, to force extensions 38, 40, 70, 72 outwardly, in the direction shown by arrows D.

Figure 13:
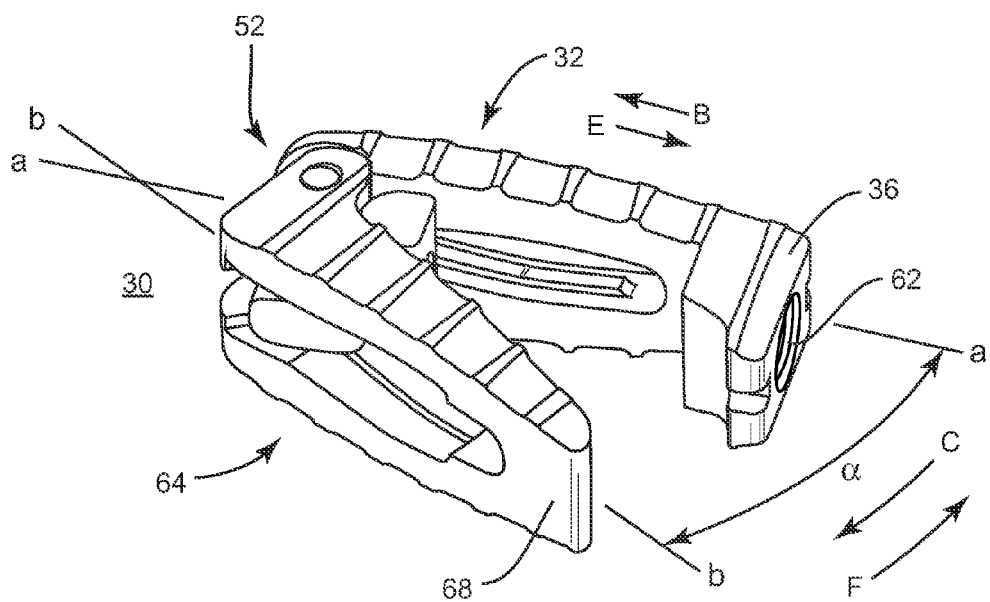
FIG. 13 is a perspective view of the spinal implant shown in FIG. 1.
Figure 14:
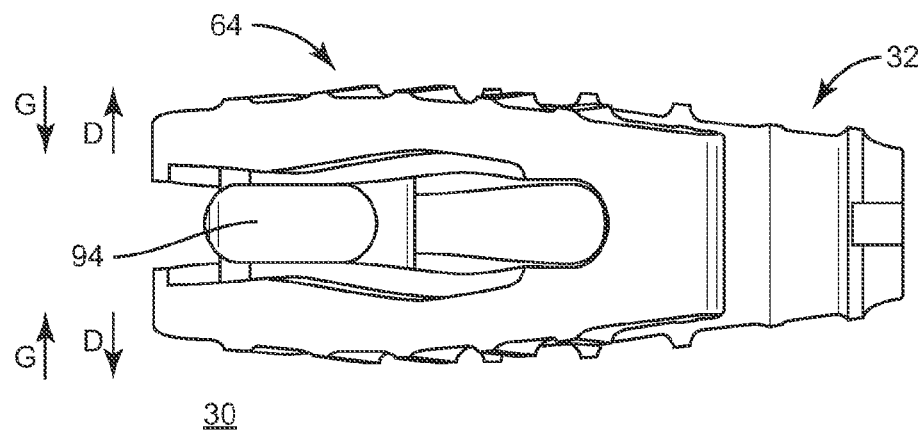
FIG. 14 is a side view of the spinal implant shown in FIG. 1.
Figure 15:
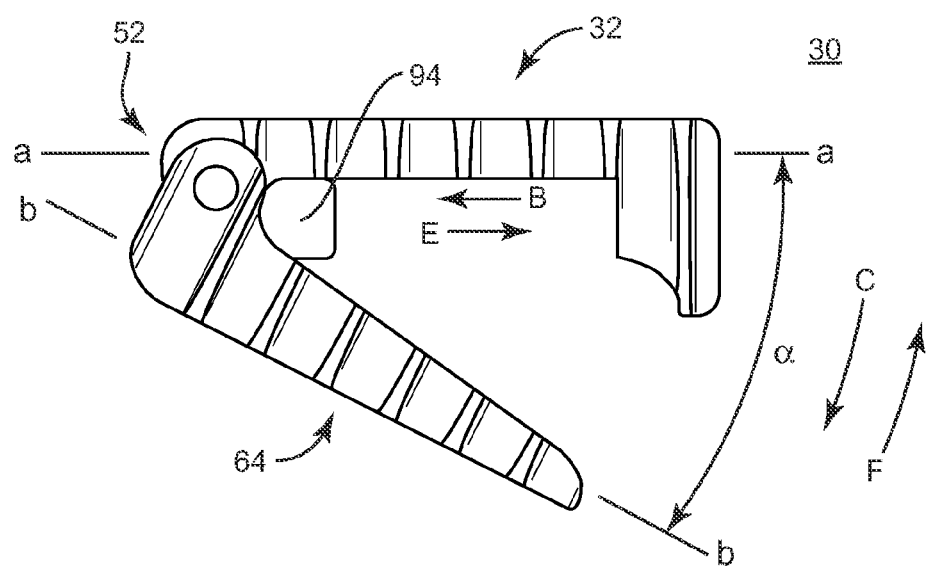
FIG. 15 is a top view of the spinal implant shown in FIG. 1.

Extensions 38, 40, 70, 72 are caused to pivot relative to their respective ends and expand such that surfaces 42, 74 are further spaced apart. Expansion of extensions 38, 40, 70, 72 causes end portions 48, 50, discs 54, 56 and end portions 80, 82, respectively, to expand and become further spaced apart. Wedge 94 is translated axially to a second configuration of spinal implant 30, such as, for example, an expanded configuration as shown in FIGS. 13-15, such that spinal implant 30 expands in a plurality of orientations relative to axis a. It is contemplated that such expansion in a plurality of orientations relative to axis a includes orientation of arm 64 along axis b relative to axis a and outward orientation of extension 38, 40, 70, 72, singly or in combination, relative to axis a.

In the expanded configuration, wings 98, 100 are disposed in a distal most position of cavities 44, 76 and ends 112, 114 are disposed in a distal most position of cavities 81, 83, relative to ends 36, 68. It is contemplated that in the expanded configuration, spinal implant 30 provides vertical and lateral expansion to increase vertical spacing in a body cavity and increase the body cavity area occupied by spinal implant 30 and provide rigid support.

In one embodiment, spinal implant 30 can be collapsed from the expanded configuration to an alternate configuration between the expanded and collapsed configurations, via manipulation of wedge 94 in a second axial direction, opposite to the first axial direction, as shown by arrow E. It is envisioned that reciprocal axial movement of wedge 94 to collapse spinal implant 30 may be desired to reposition or remove spinal implant 30 from a body cavity. Upon disposal of spinal implant 30 in the expanded configuration, to dispose spinal implant in an alternate configuration, actuator 134 is manipulated with a pulling force to retract wedge 94 axially in the second, opposite axial direction as shown by arrow E.

As wedge 94 is translated axially in the second axial direction, grooves 106, 108 slidably move along ridges 46, 47 and arm 32 remains fixed in position with regard to a body cavity of a patient. Protrusions 102, 104 slidably move within slots 78, 79 to force arm 64 inwardly and to rotate, in the direction shown by arrow F, relative to arm 32. Arm 64 pivots about the connection of arm 64 with arm 32 via hinge 52. Simultaneously, as wedge 94 is translated axially in the second axial direction, wings 98, 100 translate axially through cavities 44, 76 such that extensions 38, 40, 70, 72 collapse, in the direction shown by arrows G.

Extensions 38, 40, 70, 72 are caused to pivot relative to ends 36, 68 and collapse such that surfaces 42, 74 are brought adjacent and in close proximity. Collapse of extensions 38, 40, 70, 72 causes end portions 48, 50, discs 54, 56 and end portions 80, 82, respectively, to collapse and become disposed in close proximity. Wedge 94 is translated axially to collapse spinal implant 30 in the plurality of orientations relative to axis a toward the collapsed configuration, as described above. It is contemplated that spinal implant 30 can be manipulated to a plurality of orientations between a first configuration and a second configuration, for example, according to the position of wedge 94 along cavity 42 and axis a. It is contemplated that spinal implant 30, in the orientations described herein, may have alternate configurations, such as, for example, cage, semi-rigid or rigid body and/or flexible body.

In one embodiment, the interbody implant system includes a plurality of spinal implants 30. It is contemplated that each of the plurality of spinal implants 30 may have various cross section geometry and material configurations relative to other spinal implants 30, and the plurality of spinal implants 30 may have various orientation configurations relative to other spinal implants 30.

In assembly, operation and use, the interbody implant system is employed with a surgical procedure, such as, a fusion treatment of a spine of a patient including vertebrae V, intervertebral disc space I and body areas adjacent thereto, as discussed herein. The interbody implant system may also be employed with other surgical procedures, such as, for example, discectomy, laminotomy, laminectomy, nerve root retraction, foramenotomy, facetectomy, decompression, and spinal, nucleus or disc replacement.

For example, as shown in FIGS. 16-19 the interbody implant system can be employed with a surgical arthrodesis procedure, such as, for example, an interbody fusion for treatment of an applicable condition or injury of an affected section of a spinal column and adjacent areas within a body, such as, for example, intervertebral disc space I between first vertebrae $V_1$ and second vertebrae $V_2$ of vertebrae V. It is contemplated that spinal implant 30 of the interbody implant system, described above, can be inserted with intervertebral disc space I to space apart articular joint surfaces, provide support and maximize stabilization of vertebrae V.

In use, to treat the affected section of vertebrae V, a medical practitioner obtains access to a surgical site including vertebrae V in any appropriate manner, such as through incision and retraction of tissues. It is envisioned that the interbody implant system can be used in any existing surgical method or technique including open surgery, mini-open surgery, minimally invasive surgery and percutaneous surgical implantation, whereby vertebrae V is accessed through a mini-incision, or sleeve that provides a protected passageway to the area. Once access to the surgical site is obtained, the particular surgical procedure is performed for treating the spine disorder. Spinal implant 30, described above with regard to FIGS. 1-15, is then employed to augment the surgical treatment. Spinal implant 30 can be delivered or implanted as a pre-assembled device or can be assembled in situ. Spinal implant 30 can be completely or partially revised, removed or replaced in situ. It is contemplated that one or all of the components of the interbody implant system can be delivered to the surgical site via manual manipulation and/or a free hand technique. It is further contemplated that spinal implant 30 may be inserted posteriorly, and then manipulated anteriorly and/or lateral and/or medial.

Figure 16:
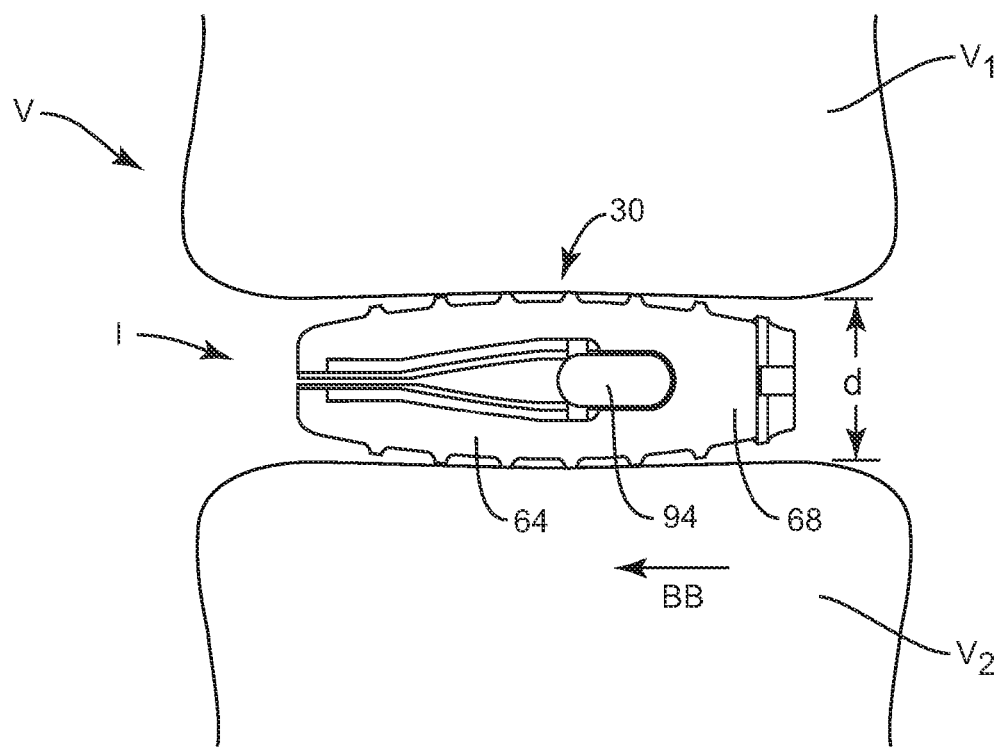
FIG. 16 is a side view of the spinal implant shown in FIG. 1 disposed with vertebrae.

An incision is made in the body of a patient and a cutting instrument (not shown) creates a surgical pathway (not shown) for implantation of spinal implant 30 within the patient body. A guide instrument (not shown) is employed to initially distract vertebrae $V_1$ from vertebrae $V_2$ a distance d, as shown in FIG. 16. A sleeve or cannula (not shown) is used to access intervertebral disc space I and facilitate delivery and access for components of the interbody implant system. A preparation instrument (not shown) can be inserted within the sleeve or cannula and disposed within intervertebral disc space I. The preparation instrument(s) can be employed to remove some or all of the disc tissue including the disc nucleus and fluids, adjacent tissues and/or bone, corticate, scrape and/or remove tissue from the surfaces of endplates of opposing vertebrae $V_1$, $V_2$, as well as for aspiration and irrigation of the region according to the requirements of a particular surgical application.

Figure 17:
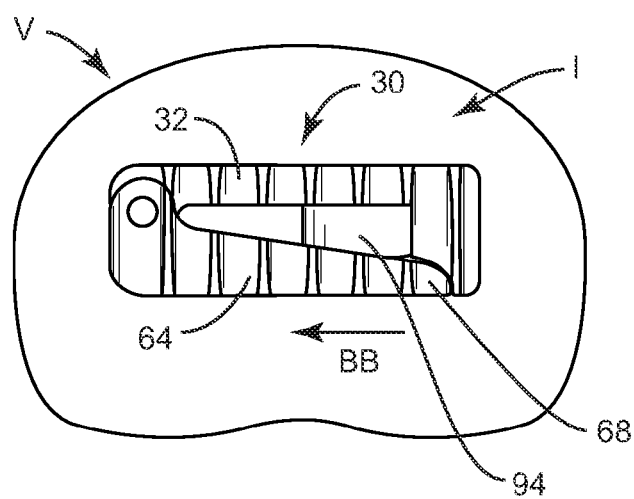
FIG. 17 is a top view of the spinal implant shown in FIG. 1 disposed with vertebrae.

As shown in FIGS. 16-17, spinal implant 30 is disposed in the first, collapsed configuration, described above and delivered through the surgical pathway along a direct lateral approach into intervertebral disc space I with a delivery instrument (not shown) including a driver (not shown). The driver delivers spinal implant 30 into the prepared intervertebral disc space I, between vertebrae $V_1$ and vertebrae $V_2$, according to the requirements of a particular surgical application. Instrument 118, described above, is delivered to the surgical site adjacent intervertebral disc space I and threaded portion 130 (FIG. 9) is threaded with opening 62 such that first engagement member 126 is fixed with arm 32 to position spinal implant 30 with intervertebral disc space I.

Threaded portion 136 (FIG. 9) is threaded with opening 116 such that actuator 134 causes axial translation of wedge 94 for reciprocal movement relative to arms 32, 64, as described above. Upon desired positioning of spinal implant 30, actuator 134 is manipulated with a pushing force to drive wedge 94 axially in a first axial direction as shown by arrow BB in FIGS. 16-17. Arm 64 is forced outwardly and rotates, in the angular direction as shown by arrow CC in FIG. 19, relative to arm 32. Arm 64 pivots about the connection of arm 64 with arm 32 via hinge 52. Simultaneously, as wedge 94 is translated axially in the first axial direction, extensions 38, 40, 70, 72 (FIGS. 2-3) are forced outwardly, as described above, in the direction shown by arrows DD in FIG. 18.

Figure 18:
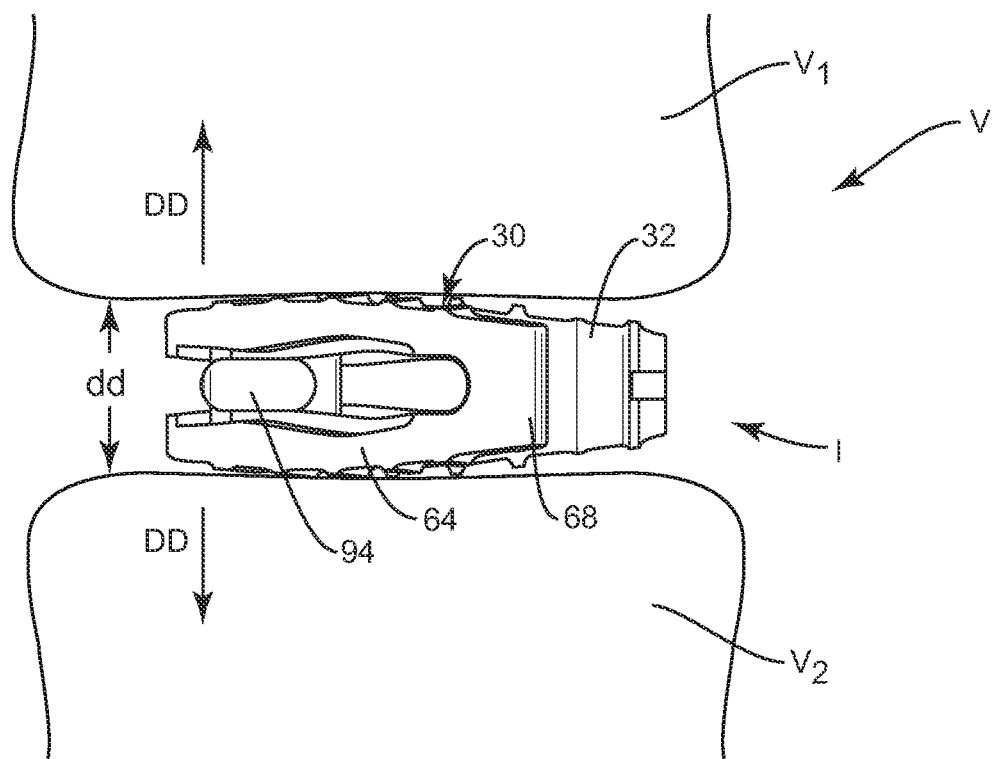
FIG. 18 is a side view of the spinal implant shown in FIG. 1 disposed with vertebrae.
Figure 19:
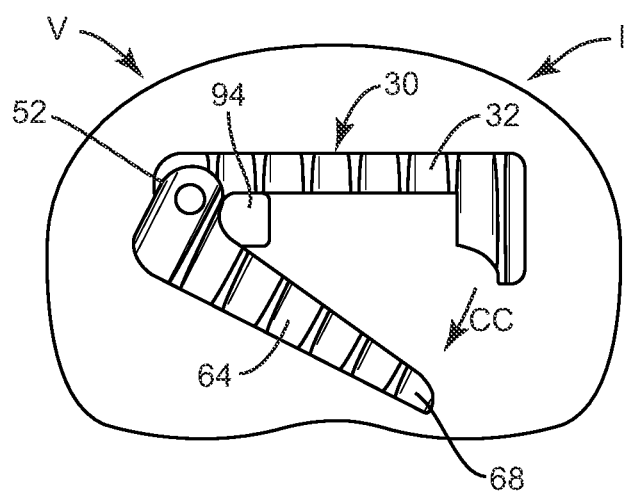
FIG. 19 is a top view of the spinal implant shown in FIG. 1 disposed with vertebrae.

Wedge 94 is translated axially to a second, expanded configuration of spinal implant 30, as shown in FIGS. 18-19, such that spinal implant 30 expands in a plurality of orientations and vertebrae $V_1$, $V_2$ are distracted a distance dd. It is contemplated that in the expanded configuration, spinal implant 30 provides vertical and lateral expansion to increase vertical spacing of intervertebral disc space I and increase the disc space area occupied by spinal implant 30, and provide rigid support. It is further contemplated that in the expanded configuration, spinal implant 30 expands in height to achieve decompression and the restoration of lordosis, and expands laterally to resist subsidence.

Figure 20:
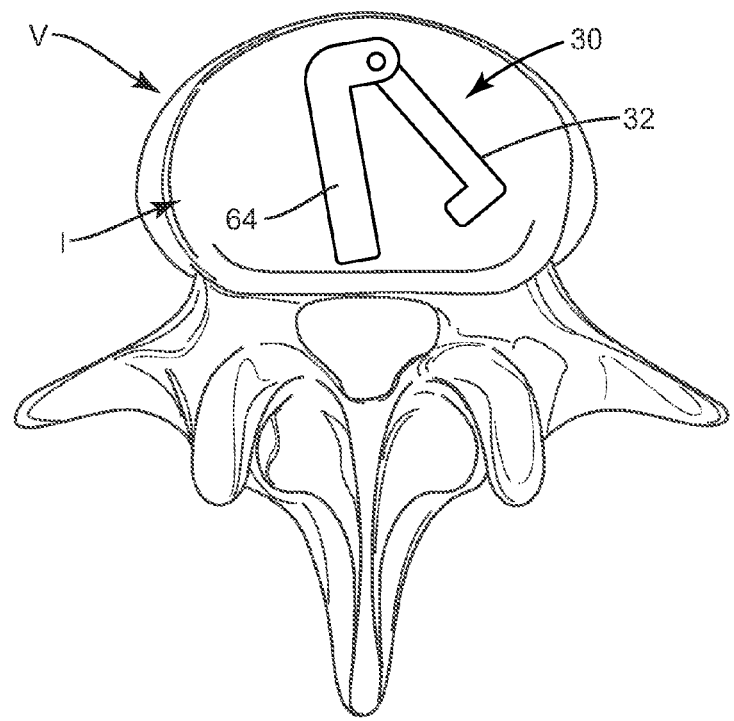
FIG. 20 is a top view of one embodiment of a spinal implant of the system disposed with vertebrae in accordance with the principles of the present disclosure.
Figure 21:
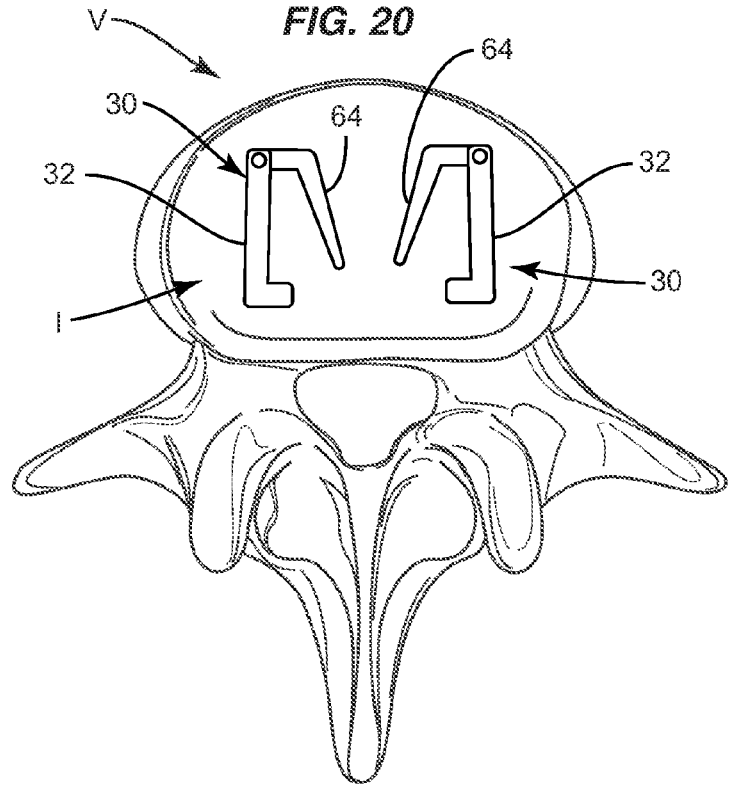
FIG. 21 is a top view of one embodiment of a spinal implant of the system disposed with vertebrae in accordance with the principles of the present disclosure.
Figure 22:
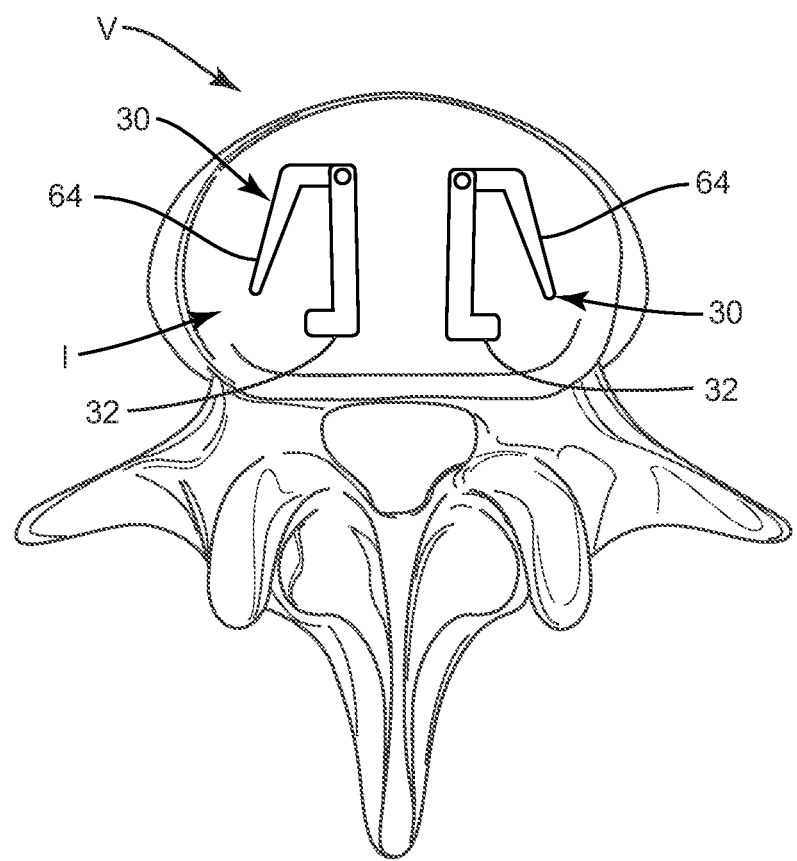
FIG. 22 is a top view of one embodiment of a spinal implant of the system disposed with vertebrae in accordance with the principles of the present disclosure.

It is envisioned that the components of the interbody implant system, which may include one or a plurality of spinal implants 30, can be delivered to the surgical site via alternate approaches. In one embodiment, as shown in FIG. 20, a spinal implant 30, described above with regard to FIGS. 1-19, is delivered through the surgical pathway along a transforaminal lumbar interbody fusion approach into intervertebral disc space I and disposed in the expanded configuration. In one embodiment, as shown in FIG. 21, a pair of spinal implants 30, described above with regard to FIGS. 1-19, are delivered through the surgical pathway along a posterior lumbar interbody fusion (PLIF) approach into intervertebral disc space I and disposed in the expanded configuration in a side by side orientation such that arms 64 are in adjacent relation. In one embodiment, as shown in FIG. 22, a pair of spinal implants 30, similar to that described above with regard to FIG. 21, are delivered through the surgical pathway along a PLIF approach into intervertebral disc space I and disposed in the expanded configuration in a side by side orientation such that arms 32 are in adjacent relation.

In one embodiment, spinal implant 30 can be collapsed from the expanded configuration to an alternate configuration between the expanded and collapsed configurations, via manipulation of wedge 94 in a second axial direction, opposite to the first axial direction, as described above, to collapse spinal implant 30 as may be desired to reposition with or remove spinal implant 30 from intervertebral disc space I. In one embodiment, the interbody implant system includes a plurality of spinal implants 30, which can be variously sized and configured, and/or oriented in a side by side engagement, spaced apart and/or staggered.

In one embodiment, the interbody implant system includes an agent, which includes a bone growth promoting material, which may be disposed, packed or layered within, on or about the components and/or surfaces thereof. The bone growth promoting material, such as, for example, bone graft can be a particulate material, which may include an osteoconductive material such as hydroxyapatite and/or an osteoinductive agent such as a bone morphogenic protein (BMP) to enhance bony fixation of spinal implant 30 with the adjacent vertebrae V.

It is contemplated that the bone graft may include therapeutic polynucleotides or polypeptides. It is further contemplated that the bone graft may include biocompatible materials, such as, for example, biocompatible metals and/or rigid polymers, such as, titanium elements, metal powders of titanium or titanium compositions, sterile bone materials, such as allograft or xenograft materials, synthetic bone materials such as coral and calcium compositions, such as hydroxyapatite, calcium phosphate and calcium sulfite, biologically active agents, for example, gradual release compositions such as by blending in a bioresorbable polymer that releases the biologically active agent or agents in an appropriate time dependent fashion as the polymer degrades within the patient. Suitable biologically active agents include, for example, BMP, Growth and Differentiation Factors proteins (GDF) and cytokines.

Spinal implant 30 can be made of radiolucent materials such as polymers. Radiomarkers may be included for identification under x-ray, fluoroscopy, CT or other imaging techniques.

It is envisioned that the agent may include one or a plurality of therapeutic agents and/or pharmacological agents for release, including sustained release, to treat, for example, pain, inflammation and degeneration. The agents may include pharmacological agents, such as, for example, antibiotics, anti-inflammatory drugs including but not limited to steroids, anti-viral and anti-retroviral compounds, therapeutic proteins or peptides, therapeutic nucleic acids (as naked plasmid or a component of an integrating or non-integrating gene therapy vector system), and combinations thereof.

The agent may also include analgesics or anesthetics such as acetic acid derivatives, COX-2 selective inhibitors, COX-2 inhibitors, enolic acid derivatives, propionic acid derivatives, salicylic acid derivatives, opioids, opioid/nonopioid combination products, adjuvant analgesics, and general and regional/local anesthetics.

The agent may also include antibiotics such as, for example, amoxicillin, beta-lactamases, aminoglycosides, beta-lactam (glycopeptide), clindamycin, chloramphenicol, cephalosporins, ciprofloxacin, erythromycin, fluoroquinolones, macrolides, metronidazole, penicillins, quinolones, rapamycin, rifampin, streptomycin, sulfonamide, tetracyclines, trimethoprim, trimethoprim-sulfamthoxazole, and vancomycin.

The agent may also include immunosuppressives agents, such as, for example, steroids, cyclosporine, cyclosporine analogs, cyclophosphamide, methylprednisone, prednisone, azathioprine, FK-506, 15-deoxyspergualin, prednisolone, methotrexate, thalidomide, methoxsalen, rapamycin, leflunomide, mizoribine (Bredinin™), brequinar, deoxyspergualin, and azaspirane (SKF 105685), Orthoclone OKT™ 3 (muromonab-CD3). Sandimmune™, Neoral™, Sangdya™ (cyclosporine), Prograf™ (FK506, tacrolimus), Cellcept™ (mycophenolate motefil, of which the active metabolite is mycophenolic acid), Imuran™ (azathioprine), glucocorticosteroids, adrenocortical steroids such as Deltasone™ (prednisone) and Hydeltrasol™ (prednisolone), Folex™ and Mexate™ (methotrxate), Oxsoralen-Ultra™ (methoxsalen) and Rapamuen™ (sirolimus).

In one embodiment, as shown in FIGS. 23-29, the interbody implant system includes a spinal implant 230, similar to spinal implant 30 described above with regard to FIGS. 1-19. Spinal implant 230 includes a first bifurcated arm 232 extending between a first end 234 and a second end 236. Arm 232 includes a first extension 238 and a second extension 240 extending from second end 236 along a longitudinal axis aa. Extensions 238, 240 are connected via a hinge 350 to facilitate pivoting and/or rotation of extensions 238, 240 relative to second end 236, and pivoting and/or rotation of extension 238 relative to extension 240.

Extensions 238, 240 include a surface 242 that defines an inner cavity 244. Cavity 244 is elongated along axis aa, and expands and collapses with spinal implant 230, as will be described. Extension 238 defines a vertebra engaging surface 239 configured to engage with vertebral tissue. Extension 240 defines a vertebra engaging surface 243 configured to engage with vertebral tissue.

First end 234 includes end portions 248, 250 of extensions 238, 240, respectively. First end 234 defines a portion of an expandable bifurcated hinge 252. Hinge 252 includes a first hinge 254 and a second hinge 256, which are configured for connecting first arm 232 with a second component, described below. Hinge 252 expands and collapses with spinal implant 230, as will be described.

Spinal implant 230 includes a second component, such as, for example, a second bifurcated arm 264, which extends between a first end 266 and a second end 268. Arm 264 includes a first extension 270 and a second extension 272 extending from second end 268 along an axis bb, which is disposed relative to axis aa as a component of spinal implant 230. Extensions 270, 272 are connected via a hinge 352 to facilitate pivoting and/or rotation of extensions 270, 272 relative to second end 268, and pivoting and/or rotation of extension 270 relative to extension 272. Hinges 350, 352 facilitate expansion and collapse of the extensions of arms 232, 264 with spinal implant 230, as will be described.

Extensions 270, 272 include a surface 274 that defines an inner cavity 276. Cavity 276 is elongated along axis bb and expands and collapses with spinal implant 230, as will be described. Extension 270 defines a vertebra engaging surface 271 configured to engage with vertebral tissue. Extension 272 defines a vertebra engaging surface 275 configured to engage with vertebral tissue.

Extension 270 and extension 238 define a cavity 281 disposed therebetween. Cavity 281 is elongated and extends between the first and second ends of arms 232, 264. Extension 272 and extension 240 define a cavity 283 disposed therebetween. Cavity 283 is elongated and extends between the first and second ends of arms 232, 264.

First end 266 includes end portions 280, 282 of extensions 270, 272, respectively. First end 266 defines a portion of expandable bifurcated hinge 252, which includes hinges 254, 256 configured for connecting first arm 232 with second arm 264. Hinge 252 facilitates a pivoting connection between arms 232, 264. Arms 232, 264 are relatively movable such that the end portions and the extensions of arms 232, 264 expand and collapse with spinal implant 230, as will be described. Second end 268 is rotatable, via the pivotable connection of arms 232, 264 with hinge 252, to an angular orientation relative to axis aa corresponding to the expansion of spinal implant 230.

An intermediate component, such as, for example, a wedge 294 is engageable with arm 232 and arm 264. Wedge 294 is disposed with arms 232, 264 such that at least a portion of wedge 294 is disposed within cavities 244, 276. Wedge 294 includes a first member 296 having wings 298, 300. Wing 298 extends through cavity 244 and is slidably supported therein by surface 242. Wing 300 extends through cavity 276 and is slidably supported therein by surface 274.

First member 296 is disposed in a horizontal plane such that first member 296 is able to freely slide between arms 232, 264 and their respective extensions.

Wedge 294 includes a second member 310 connected with and disposed in a transverse orientation relative to first member 296. Second member 310 has ends 312, 314. End 312 extends through cavity 281 and is slidably supported therein by extensions 238, 270. Wing 314 extends through cavity 283 and is slidably supported therein by extensions 240, 272. Second member 310 is disposed in a transverse plane to the plane defined by first member 296 such that second member 310 is able to freely slide between arms 232, 264 and their respective extensions.

In operation, spinal implant 230 is engaged for disposal between a first configuration and a second configuration such that spinal implant 230 expands in a plurality of orientations relative to axis aa. Spinal implant 230 is engaged with an instrument (not shown), similar to that described above, to facilitate actuation of the component parts of spinal implant 230 and disposal thereof in various configurations according to the requirements of a particular surgical application.

Figure 23:
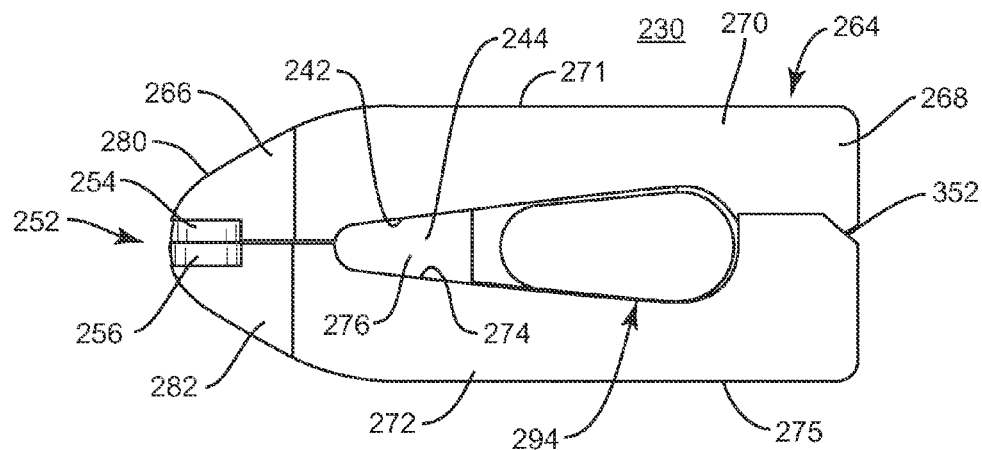
FIG. 23 is a side view of one embodiment of a spinal implant of the system in accordance with the principles of the present disclosure.
Figure 24:
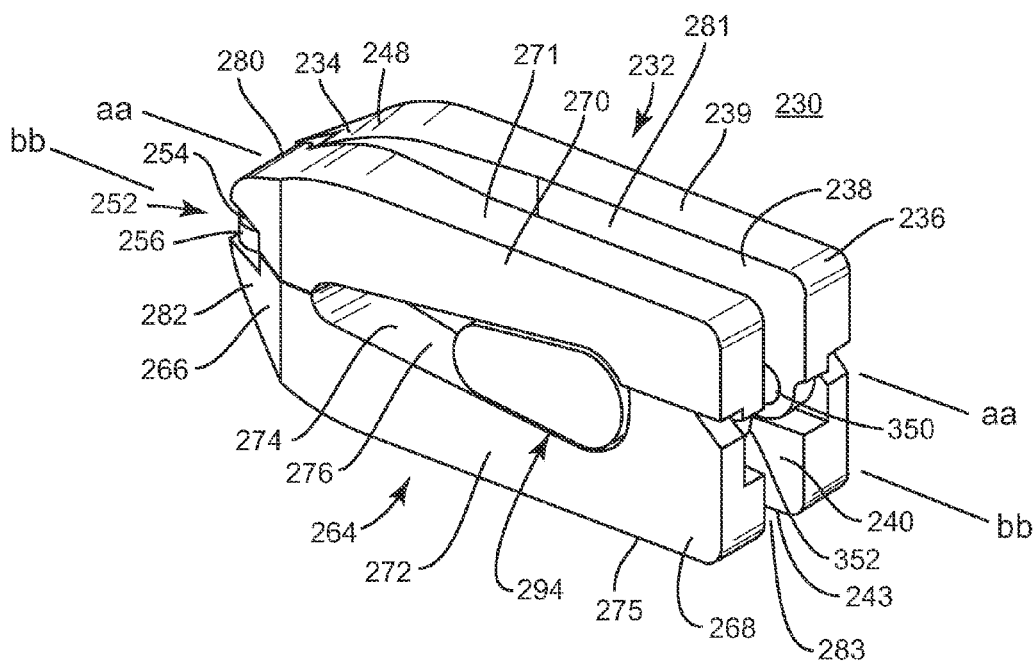
FIG. 24 is a perspective view of the spinal implant shown in FIG. 23.
Figure 25:
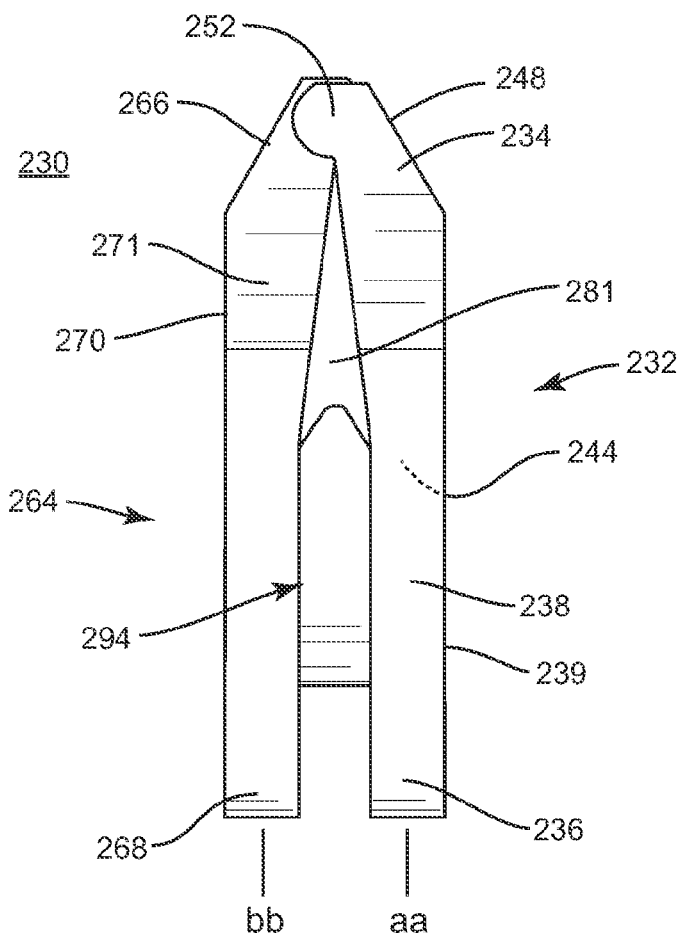
FIG. 25 is a top view of the spinal implant shown in FIG. 23.
Figure 26:
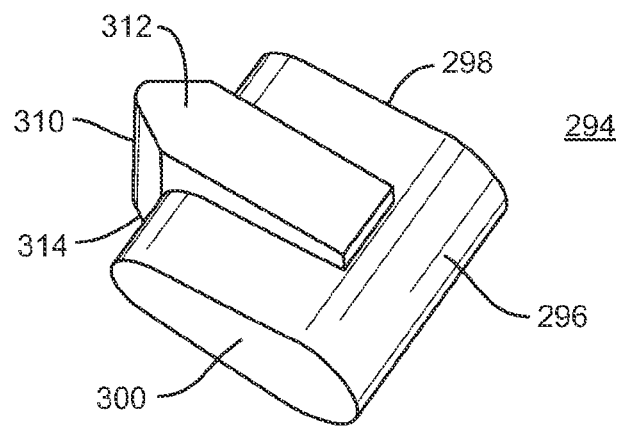
FIG. 26 is a perspective view of an intermediate component of the spinal implant shown in FIG. 23.

In a collapsed configuration, as shown in FIGS. 23-25, arms 232, 264 are disposed in a low profile orientation such that axis bb, corresponding to the positioning of arm 264, is disposed in substantially parallel relation to axis aa, corresponding to arm 232. Second end 268 is disposed adjacent and in close proximity to second end 236. Wedge 294 is mounted within spinal implant 230 and disposed between arms 232, 264. Wings 298, 300 are disposed in a proximal most position of cavities 244, 276 and ends 312, 314 are disposed in a proximal most position of cavities 281, 283, relative to ends 236, 268. End portions 248, 250, 280, 282, respectively, are disposed adjacent and in close proximity.

The surgical instrument is manipulable so that wedge 294 can be translated axially for reciprocal movement relative to arms 232, 264 along axis aa. Upon desired positioning of spinal implant 230, the surgical instrument is manipulated with a pushing force to drive wedge 294 axially in a first axial direction shown by arrow X in FIGS. 27-28.

Figure 27:
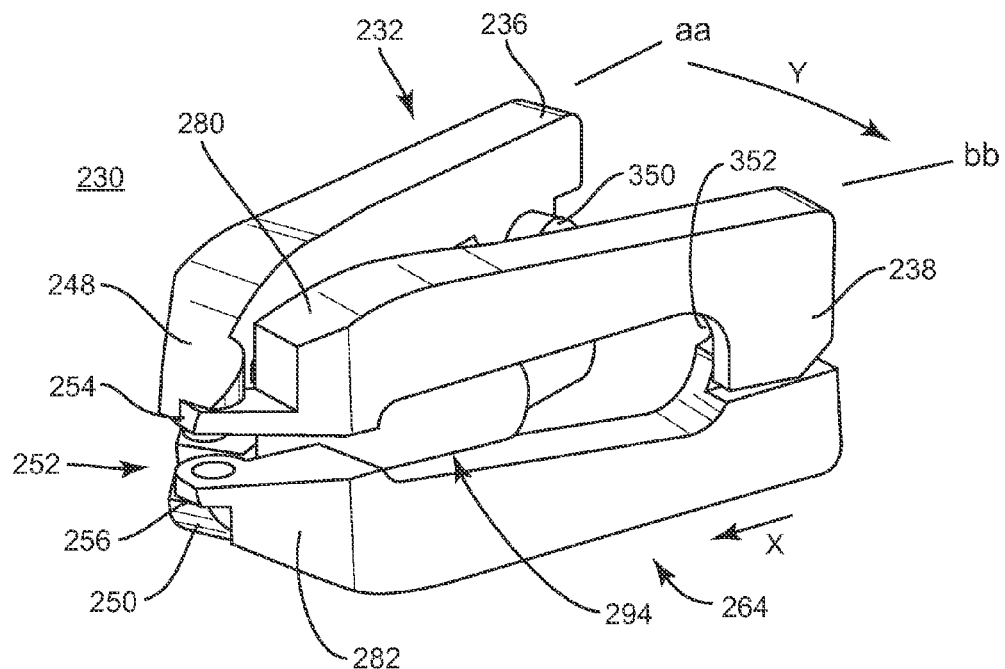
FIG. 27 is a perspective view of the spinal implant shown in FIG. 23.
Figure 28:
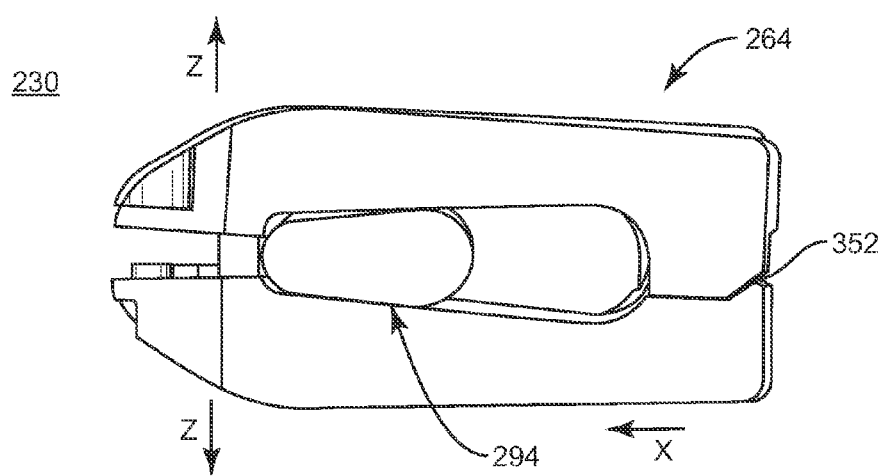
FIG. 28 is a side view of the spinal implant shown in FIG. 23.
Figure 29:
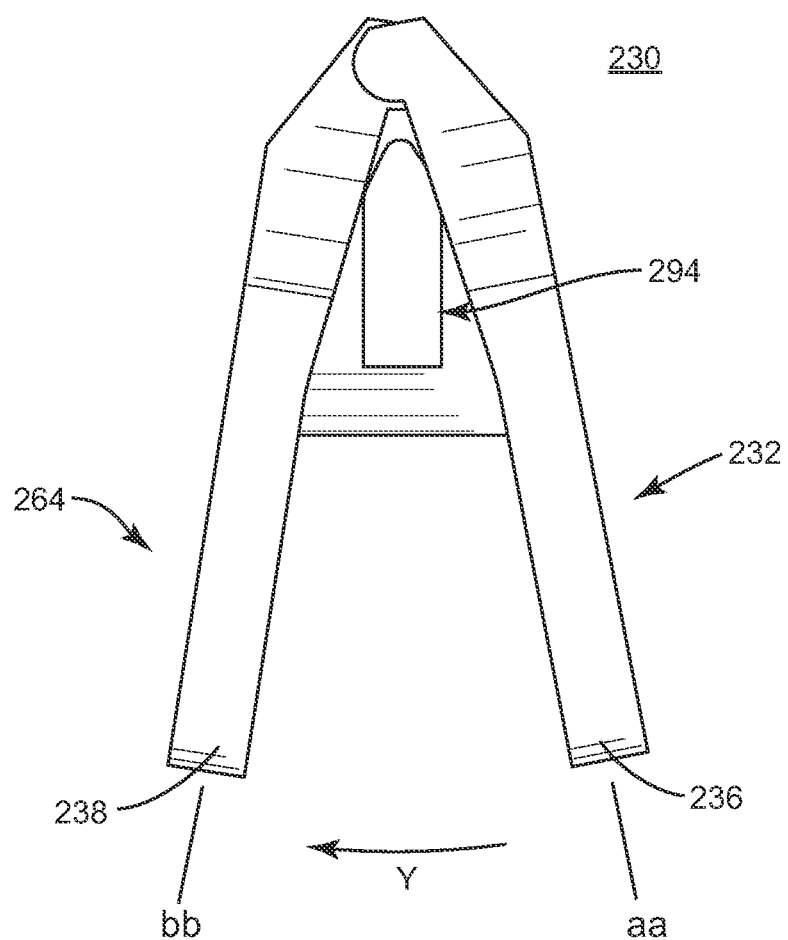
FIG. 29 is a top view of the spinal implant shown in FIG. 23.

Ends 312, 314 slidably move within cavities 281, 283, respectively to force arm 264 outwardly and to rotate, in the direction shown by arrow Y in FIGS. 27 and 29, relative to arm 232. Arm 264 pivots about the connection of arm 264 with arm 232 via hinge 252. Simultaneously, as wedge 294 is translated axially in the first axial direction, wings 298, 300 translate axially through cavities 244, 276 and engage surfaces 242, 274, respectively, to force extensions 238, 240, 270, 272 outwardly, in the direction shown by arrows Z in FIG. 28. Extensions 238, 240, 270, 272 are caused to pivot relative to ends 236, 268 and expand such that surfaces 242, 274 are further spaced apart. Expansion of extensions 238, 240, 270, 272 causes end portions 248, 250, 280, 282, respectively, to expand and become further spaced apart. Wedge 294 is translated axially to the expanded configuration of spinal implant 230 as shown in FIGS. 27-29, such that spinal implant 230 expands in a plurality of orientations relative to axis aa. It is contemplated that such expansion in a plurality of orientations relative to axis aa includes orientation of arm 264 along axis bb relative to axis aa and outward orientation of extensions 238, 240, 270, 272, singly or in combination, relative to axis aa.

In the expanded configuration, wings 298, 300 are disposed in a distal most position of cavities 244, 276 and ends 312, 314 are disposed in a distal most position of cavities 281, 283, relative to ends 236, 268. It is contemplated that the hinges of spinal implant 230 are disposed in a triangular footprint and each hinge provides a column of rigid support in the expanded configuration. For example, hinge 252 provides a pair of hinges to increase the implant spacing and surface area support, and hinges 350, 352 provide vertical spacing to create lordosis.

In one embodiment, spinal implant 230 can be collapsed from the expanded configuration to an alternate configuration between the expanded and collapsed configurations, similar to that described above with regard to spinal implant 30. It is envisioned that the interbody implant system including spinal implant 230 may be employed with surgical procedures such as those described herein.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:
1. A spinal implant comprising:
a first component extending between a first end and a second end and defining a surface therebetween;
a second component being movable relative to the first component, the second component extending between a first end and a second end and defining a surface therebetween, the first ends of the first and second components being pivotably connected;
an intermediate component engageable with the first component and the second component, the intermediate component being configured for relative movement along the surface of the second component and being configured for relative movement along the surface of the first component in a first axial direction from a first position adjacent the second ends of the components to a second position adjacent the first ends of the components such that movement of the intermediate component from the first position to the second position rotates the second end of the second component relative to the second end of the first component about the first ends of the components;
wherein the surface of the first component defines a ridge extending outwardly therefrom along a longitudinal axis of the implant, the intermediate component defining a cavity configured for relative movement along the wall in the first axial direction and a second, opposite axial direction while receiving the ridge within the cavity; and
wherein the surface of the second component defines a passageway extending along the longitudinal axis of the implant, the passageway being recessed within the surface of the second component, the intermediate component defining a protrusion configured for relative movement within the passageway.

2. The spinal implant of claim 1, wherein the first component has a bifurcated configuration including bifurcated walls and an inner cavity extending longitudinally along the first component between the bifurcated walls, the inner cavity defining the surface of the first component.

3. The spinal implant of claim 2, wherein at least a portion of the intermediate component is disposed within the inner cavity during movement between the first position and the second position.

4. The spinal implant of claim 1, wherein the second component has a bifurcated configuration including bifurcated walls and an inner cavity extending longitudinally along the second component between the bifurcated walls, the inner cavity of the second component defining the surface of the second component.

5. The spinal implant of claim 4, wherein at least a portion of the intermediate component is disposed within the inner cavity of the second component during movement between the first position and the second position.

6. The spinal implant of claim 1, wherein each of the first ends of the first and second components have a bifurcated configuration.

7. The spinal implant of claim 6, wherein, when the intermediate member is moved from the first position to the second position, the spinal implant is expanded in a plurality of orientations relative to the longitudinal axis.

8. The spinal implant of claim 1, wherein the first component is pivotably connected to the second component by a bifurcated hinge that is configured to expand as the intermediate component translates between the first and second positions.

9. The spinal implant of claim 1, wherein the first end of the first component includes a bifurcated hinge including a pair of spaced apart discs, a first disc having a first protrusion extending in a first direction and a second disc having a second protrusion extending in a second direction opposite the first direction; and the first end of the second component including a pair of openings configured for disposal of the first and second protrusions such that the protrusions are rotatable within the openings.

10. The spinal implant of claim 2, wherein a height of the inner cavity tapers between the second and first ends of the first component relative to the longitudinal axis.

11. An interbody implant system comprising:
a spinal implant defining a longitudinal axis, the implant including:
a first arm defining a surface extending between a first end and a second end, the surface including an elongated ridge extending along the longitudinal axis of the implant and protruding from the surface of the first arm,
a second arm defining a surface extending between a first end and a second end, the first end of the second arm being pivotably connected to the first end of the first arm, the surface of the second arm including a slot extending along the longitudinal axis of the implant, the slot extending into the surface of the second arm, and
a wedge defining a cavity, the wedge being engageable with the first arm and the second arm, the wedge including a protrusion configured for relative slidable movement along the slot and along the longitudinal axis of the implant when the protrusion is received within the slot, and the wedge defining a groove configured for relative slidable movement along the ridge and along the longitudinal axis of the implant when the ridge is received within the groove, the wedge capable of relative slidable movement from a first position adjacent the second ends of the first and second arms to a second position adjacent the first ends of the first and second arms such that movement of the wedge from the first position to the second position pivots the second end of the second arm relative to the second end of the first arm between a collapsed configuration and an expanded configuration of the spinal implant; and an instrument including an engagement member being engageable with the cavity to cause movement of the wedge.

12. The spinal implant of claim 11, wherein the first arm has a bifurcated configuration that includes bifurcated walls and an inner cavity between the bifurcated walls along the surface of the first arm.

13. The spinal implant of claim 11, wherein the first end of the second arm is pivotably connected to the first end of the first arm by an expandable bifurcated hinge.

14. The spinal implant of claim 11, wherein as the wedge translates from the first position to the second position the spinal implant is expanded in a plurality of orientations relative to the longitudinal axis.

15. The spinal implant of claim 11, wherein the wedge is reciprocally movable longitudinally along the surface of the first arm along the longitudinal axis of the implant.

16. The spinal implant of claim 11, wherein the instrument includes an outer engagement member coaxially disposed with the engagement member and configured for fixation with the first arm such that the engagement member axially moves the wedge relative to the first arm.

17. An interbody implant system comprising:
a spinal implant defining a longitudinal axis, the implant including:
a first bifurcated arm extending along the longitudinal axis between a first end and a second end, the first arm including a surface that defines an inner cavity and an elongated ridge extending along the longitudinal axis, the second end defining a cavity,
a second bifurcated arm extending along the longitudinal axis between a first end and a second end, the second arm including a surface that defines an inner cavity and a slot extending along the longitudinal axis, the first end of the second arm being pivotably connected to the first end of the first arm via an expandable bifurcated hinge, and
a wedge defining a second cavity and being disposed within the first arm and the second arm such that at least a portion thereof is disposed within the inner cavities of the arms, the wedge including a protrusion configured for relative slidable movement along the slot and along the longitudinal axis, and the wedge defining a groove configured for relative slidable movement along the ridge and along the longitudinal axis from a first position adjacent the second ends of the arms to a second position adjacent the first ends of the arms such that movement of the wedge from the first position to the second position pivots the second arm relative to the first arm between a collapsed configuration and an expanded configuration such that the spinal implant expands in a plurality of orientations relative to the longitudinal axis as the wedge is moved from the first position to the second position; and an instrument including a first engagement member and a second engagement member coaxially disposed within the first engagement member, the first engagement member being engageable with the second cavity of the wedge and the second engagement member being engageable with the cavity of the first arm such that the second engagement member axially facilitates movement of the wedge relative to the first arm in a first axial direction from the first position to the second position and a second opposite axial direction from the second position to the first position along the longitudinal axis.

* * * * *